(12) United States Patent
Kubin

(10) Patent No.: US 12,150,993 B2
(45) Date of Patent: Nov. 26, 2024

(54) HYPERICIN-PVP COMPLEX WITH HIGH HYPERICIN CONTENT

(71) Applicant: Hypericum LifeScience GmbH, Vienna (AT)

(72) Inventor: Andreas Kubin, Vienna (AT)

(73) Assignee: HYPERICUM LIFESCIENCE GMBH, Vienna (AT)

( * ) Notice: Subject to any disclaimer, the term of this patent is extended or adjusted under 35 U.S.C. 154(b) by 990 days.

(21) Appl. No.: 17/255,349

(22) PCT Filed: Jul. 12, 2019

(86) PCT No.: PCT/EP2019/068775
§ 371 (c)(1),
(2) Date: Dec. 22, 2020

(87) PCT Pub. No.: WO2020/011960
PCT Pub. Date: Jan. 16, 2020

(65) Prior Publication Data
US 2021/0260192 A1    Aug. 26, 2021

(30) Foreign Application Priority Data
Jul. 13, 2018 (EP) .................... 18183435

(51) Int. Cl.
| A61K 41/00 | (2020.01) |
| A01N 25/10 | (2006.01) |
| A01N 35/04 | (2006.01) |
| A61K 47/58 | (2017.01) |

(52) U.S. Cl.
CPC .......... *A61K 41/0057* (2013.01); *A01N 25/10* (2013.01); *A01N 35/04* (2013.01); *A61K 47/58* (2017.08)

(58) Field of Classification Search
None
See application file for complete search history.

(56) References Cited

U.S. PATENT DOCUMENTS

| 2006/0127349 A1 | 6/2006 | Kubin et al. |
| 2018/0055935 A1 | 3/2018 | Welzig et al. |

FOREIGN PATENT DOCUMENTS

| JP | 201335819 | 2/2013 |
| WO | WO 2001/089576 | 11/2001 |
| WO | WO 2014/079972 | 5/2014 |
| WO | WO 2017/054017 | 4/2017 |
| WO | WO 2017/054018 | 4/2017 |

OTHER PUBLICATIONS

Extended European Search Report issued in European Patent Application No. 18183435.9, dated Jan. 16, 2019.
Feinweber, et al. "Applicability of new degradable hypericin-polymer-conjugates as photosensitizers: principal mode of action demonstrated by in vitro models," *Photochemical & Photobiological Sciences*, 2014, 13:1607-1620.
Freytag, "Determination of hypericin and detection of pseudohypericin in Hypericum perforatum by high-pressure liquid chromatography," *Deutsche Apotheker Zeitung, DT.*, 1984, 124(46):2383-2386.
International Search Report and Written Opinion issued in International Patent Application No. PCT/EP2019/068775, dated Sep. 26, 2019.
Kapinus, et al. "Spectroscopic Investigation of the Molecular Structure of Hypericin and its Salts," *Monatshefte fur Chemie*, 1999, 130:623-635.
Kubin, et al. "Fluorescence Diagnosis of bladder Cancer with New Water Soluble Hypericin Bound to Polyvinylpyrrolidone: PVP-Hypericin," *Photochemistry and Photobiology*, 2008, 84:1560-1563.
Kubin, et al. "How to make hypericin water-soluble," *Pharmazie*, 2008, 63(4):263-269.
Extended Japanese Search Report issued in corresponding Japanese Application No. 2021-502850, dated Nov. 29, 2022.
Kubin et al., "How to make hypericin water-soluble" *Pharmazie* 2008, 63: 263-269.
Office Action issued in Corresponding Japanese Application No. 2021-502850, dated May 10, 2022 (English Translation provided).

*Primary Examiner* — Samantha L Shterengarts
*Assistant Examiner* — Jed A Kucharczk
(74) *Attorney, Agent, or Firm* — Norton Rose Fulbright US LLP

(57) ABSTRACT

The invention relates to a complex that consists of hypericin or a hypericin salt and polyvinyl pyrrolidone (PVP), the average mass fraction of hypericin or hypericin salt in the entire complex being higher than 6% by weight. The invention further relates to a process for preparing said hypericin-PVP complex, according to which process a mixture of hypericin and PVP is heated to a temperature above the glass transition temperature of the PVP used.

5 Claims, 2 Drawing Sheets

HYPERICIN-PVP COMPLEX WITH HIGH HYPERICIN CONTENT

CROSS-REFERENCE TO RELATED APPLICATIONS

Figure 1:
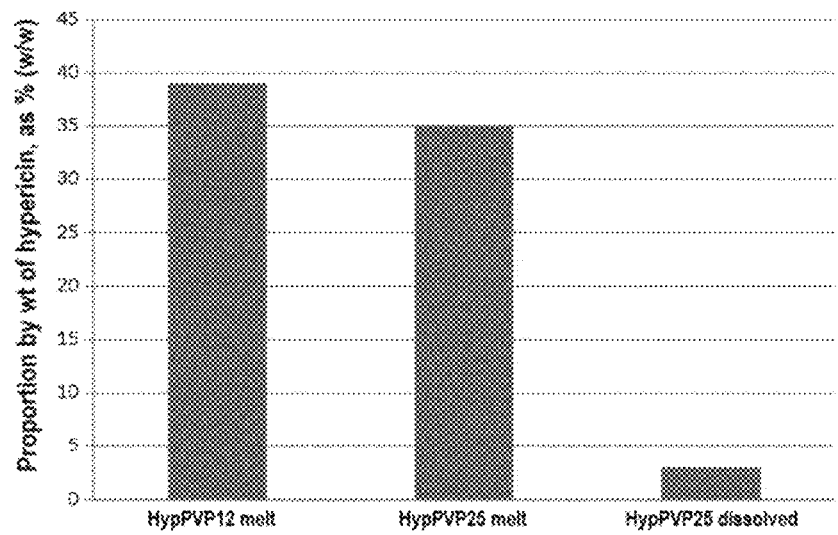

This application is a national phase application under 35 U.S.C. § 371 of International Application No. PCT/EP2019/068775 filed 12 Jul. 2019, which claims priority to European Patent Application No. 18183435.9 filed 13 Jul. 2018. The entire contents of each of the above-referenced disclosures is specifically incorporated by reference herein without disclaimer.

The present invention relates to a complex formed by hypericin or a hypericin salt and polyvinylpyrrolidone (PVP, the complex having a particularly high proportion of hypericin.

Hypericin can be found as a constituent of various plants, in particular in *hypericum* sp. and as a pigment in protozoa, in certain Australian insects and, with side chains, as fagopyrin in buckwheat.

Because of its photodynamic and photochemical properties, a variety of research projects investigating the application of the photosensitizer in tumour diagnostics and tumour therapy have focused again and again on hypericin.

In the last 50 years, photodynamic therapy (PDT) of tumours has developed on the fringes of oncology. However, the mechanisms of PDT have been extensively elucidated and methods have been defined. After systemic or local application of a photosensitizer, the photosensitizer becomes accumulated in malignant tissue. When the photosensitizer is excited with the aid of light of a suitable wavelength, it can transfer energy to a reaction partner, for example to molecular oxygen. The reactive oxygen molecules which are generated thereby can in turn damage the cellular structures of the tumour tissue.

However, until now, there has been a dearth of genuinely suitable photosensitizers which are concentrated in tumour cells, are highly compatible and meet the physical and chemical requirements for PDT. In particular, the method using delta-aminolevelunic acid (5-ALA) as a "prodrug" for protoporphyrin IX in hollow organs (stomach, intestines, bladder, lungs etc) has been developed the most. The disadvantage with 5-ALA or protoporphyrin IX is instability: porphyrins are light-sensitive and discolour during the therapy, lose concentration in the tissue and dosages are difficult to calculate.

The stability of hypericin as a photosensitizer is known, as well as the fact that this plant constituent is concentrated in tumour cells. Along with the chemical and physical properties, these are the optimal requirements for employing a sensitizer in PDT. By means of in vitro experiments, the effectiveness of hypericin in PDT has been shown in a series of cell lines and in addition, in vivo animal studies have confirmed the potential of hypericin in PDT.

Hypericin is a hydrophobic substance which is completely insoluble in water and requires the most widely different formulations in order to be able to be used for medical purposes. Formulations of this type thus contain various solvents which, however, are often not very compatible and suffer from side effects (for example alcohol, DMSO, etc) or solubilizing agents, liposomes, micelles or nanoparticles.

Firstly, WO 01/89576 A2 describes a practical approach for making hypericin soluble in water and thus capable of application by complexing with polyvinylpyrrolidone (PVP). Complexes are disclosed therein which have a molar ratio of hypericin to PVP of approximately 1:1. Page 3 discloses that hypericin and PVP can both be present in a concentration of 1 µmol/L. According to the molar mass range for PVP which is stated to be preferred in the application (10000-90000 g/mol) and the molar mass of hypericin (504.44 g/mol), this corresponds to a weight ratio of hypericin to hypericin-PVP complex of between 0.6% and 5% by weight.

Figure 3:
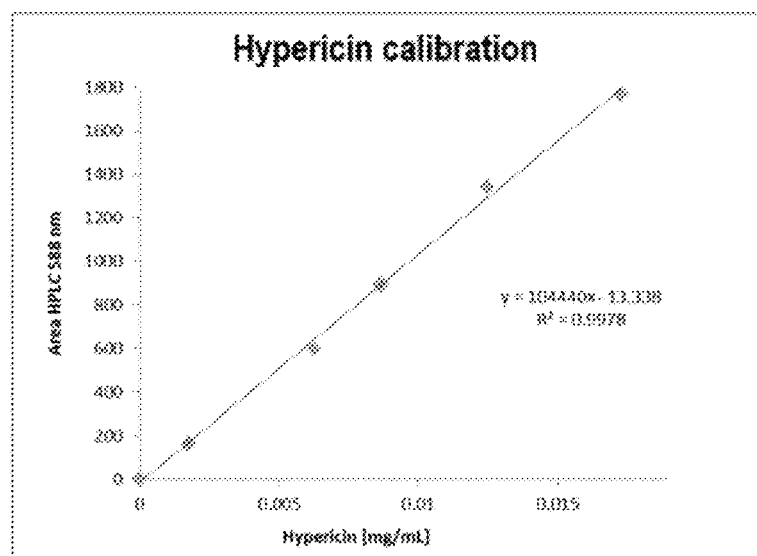

Kubin et. al. (Pharmazie 63 (2008) 263-269) describe a production method based on WO 01/89576 A2, in which hypericin which has already been dissolved in ethanol is heated with PVP and water to 70° C. and the solution obtained in this manner is then evaporated. The residue obtained then contains the water-soluble complex hypericin-PVP. In FIG. 3, a solution with a concentration of 50 µmol/L of hypericin and 100 µmol/L of PVP (PVP 10, PVP 25 or PVP 40) is disclosed. From the molar masses of hypericin (504.44 g/mol) and of PVP (10000 g/mol for PVP 10, 25000 g/mol for PVP 25, 40000 g/mol for PVP 40), the molar ratios can be converted into proportions by weight. In this manner, for the complex with PVP 10, a value of approximately 2.5% by weight is obtained, for PVP 25 a value of approximately 1% by weight is obtained and for PVP 40, a value of approximately 0.6% by weight is obtained.

Kubin et. al. (Photochemistry Photobiology 84 (2008) 1560-1563) describe a clinical study in which hypericin-PVP is used. Here, hypericin also has a proportion by weight of 1% by weight of hypericin-PVP complex.

WO 2014/079972 A1 describes equipment for PDT in hollow organs such as the bladder and mentions the use of hypericin-PVP, inter alia. The total quantity is given as 0.25 mg of hypericin bonded to 25 mg of PVP. The proportion by weight of hypericin to hypericin-PVP complex is thus at most 1% by weight.

WO 2017/054017 A1 describes hypericin formulations in the form of a salt for photodynamic therapy. In the production method for hypericin-PVP described in Example 1, 250.0 g of a phosphate buffer solution is produced which contains a total of 1875 mg of PVP k25 and 0.0225 mg of hypericin per gram of solution. The proportion by weight of hypericin in the hypericin-PVP complex is therefore 0.3% by weight.

WO 2017/054018 A1 describes hypericin formulations in the form of a salt for photodynamic diagnosis. In the production method for hypericin-PVP described in Example 1, 250.0 g of a phosphate buffer solution is produced which contains a total of 562.5 mg of PVP k25 and 0.0225 mg of hypericin per gram of solution. The proportion by weight of hypericin to hypericin-PVP complex is therefore 1% by weight.

Feinweber et al. (Photochemical & Photobiological Sciences 13.11 (2014): 1607-1620) describe conjugates consisting of hypericin and hydrolytically degradable polyphosphazenes. In order to produce non-covalent conjugates of hypericin and polydi-[2-(2-oxo-1-pyrrolidinyl)ethoxy] phosphazene (PYRP), hypericin (2.4 mg) is dissolved in 2 mL of ethanol and added to PYRP (200 mg), whereupon the solvent is removed under vacuum. As a comparison, hypericin-PVP is used, wherein that hypericin-PVP complex is produced by using PVP40 "in analogous manner". The proportion by weight of hypericin to hypericin-PVP complex is then at most 1.2% by weight.

Photodynamic diagnosis with the aid of hypericin-PVP in combination with fluorescence endoscopy as is known in the prior art is a very sensitive method and can be carried out with very small amounts of material. As has already been published many times, in the bladder, for example, only 0.25 mg of hypericin (in total 25 mg of hypericin-PVP complex containing 1% by weight of hypericin) is introduced in the dissolved form. This quantity is sufficient to stain the tumours and lesions enough for them to be identified by the urologist and for them to be able to remove them. The small proportion by weight of hypericin in the hypericin-PVP complex and the associated high proportion of PVP therefore does not cause any problems for photodynamic diagnosis because of the small amount of material used.

However, this is not the case for applications which require larger quantities of hypericin such as photodynamic therapy, for example. The higher dosage of hypericin in this case is associated with a large quantity of PVP. Thus, there is a need for hypericin-PVP complexes which contain a higher proportion of hypericin. Thus, one objective of the present invention is to provide such complexes.

This objective is achieved by means of a complex formed from hypericin or a hypericin salt and polyvinylpyrrolidone (PVP), wherein the mean proportion by weight of hypericin or of hypericin salt in the total complex is more than 6% by weight.

When "hypericin" is mentioned below, this term should be understood to include both the free acid as well as hypericin salts, preferably alkali salts, particularly preferably the sodium or potassium salt.

Water-soluble compositions can be prepared with the hypericin-PVP complex in accordance with the invention which contain large quantities of hypericin without this being associated with a disadvantageously large quantity of PVP. With this, formulations can be provided which use even less material than before. Because large quantities of adjuvants (PVP) and associated side effects can be avoided, the present invention facilitates applications which require larger quantities of hypericin. In particular, this involves therapeutic methods such as photodynamic therapy (PDT) for the treatment of tumour diseases.

Thus, the present invention also provides pharmaceutical compositions comprising the hypericin-PVP complex in accordance with the invention.

During the course of the experimental studies carried out in the context of the present invention, it was unexpectedly shown that a particularly high proportion by weight of hypericin in the hypericin-PVP complex can be obtained when a mixture of hypericin and PVP is heated to a temperature which is above the glass transition temperature of the PVP employed.

Thus, the present invention also provides a method for the production of the complex in accordance with the invention which is characterized in that a mixture of hypericin and PVP is heated to a temperature which is above the glass transition temperature of the PVP employed.

By applying this method, the inventors were able to produce hypericin-PVP complexes which contain more than 6% by weight, in particular more than 10% by weight, preferably more than 15% by weight, particularly preferably more than 20% by weight and most particularly preferably more than 35% by weight of hypericin. The proportion of hypericin in the complexes in accordance with the invention therefore significantly exceeds the proportion of hypericin in hypericin-PVP complexes of the prior art and therefore allows for novel and more advantageous applications for hypericin-PVP.

The application of the hypericin-PVP complexes to photodynamic therapy (PDT) for the treatment of tumour diseases is particularly advantageous.

Other applications as well which require larger quantities of hypericin are considerably facilitated by the present invention. As an example, in combination with light, hypericin has an antiviral and antibacterial action. The hypericin-PVP complex in accordance with the invention can thus be used for sterilising and/or disinfecting surfaces or liquids. The proportion of PVP in an application in this context remains manageably small.

Hypericin can also be described as 1,3,4,6,8,13-hexahydroxy-10,11-dimethylphenanthro[1,10,9,8-opqra]perylene-7,14-dione. Hypericin can be represented by the following structural formula (here in the form of the free acid):

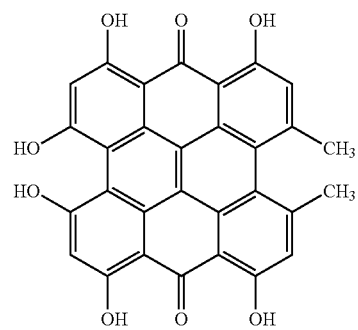 [SMILES: Cc1cc(O)c2c(=O)c3c(O)cc(O)c4c5c(O)cc(O)c6c(=O)c7c(O)cc(C)c8c1c2c(c34)c(c78)c65]

In addition to the free acid, hypericin can also be present in other forms such as in the salt form, for example alkali metal salts such as sodium or potassium salts. In the context of the present invention, the term "hypericin" describes all possible forms of this type.

Polyvinylpyrrolidone (PVP), also known as polyvidone or povidone, is a polymer of the compound vinylpyrrolidone. PVP is commercially available in different degrees of polymerization. The degree of polymerization determines the mean molar mass of the polymer.

The present invention concerns a complex formed from hypericin or a hypericin salt and polyvinylpyrrolidone (PVP), characterized in that the mean proportion by weight of hypericin or of hypericin salt in the total complex is more than 6% by weight, preferably more than 8% by weight, 10% by weight, 15% by weight, 20% by weight, 25% by weight, or more than 30% by weight.

Unless indicated otherwise, the percentages (%) given in the present invention respectively refer to the percentage by weight (% by weight). The proportion by weight here provides the relative proportion of the mass of hypericin to the mass of the whole complex (hypericin+PVP).

The proportion of hypericin in the hypericin-PVP complex can also be expressed as the molar ratio. As an example, a hypericin-PVP complex which consists of hypericin in the form of the free acid (molar mass: 504.44 g/mol) and PVP with a mean molar mass of 25 kD, and which has a mean proportion by weight of hypericin to the total complex of 10% by weight, has a mean molar ratio of hypericin to PVP in the complex of 5.5. The mean molar ratio here provides the ratio of the quantity of hypericin to the quantity of PVP.

Thus, the present invention also concerns a complex formed from hypericin and PVP, characterized in that the mean molar ratio of hypericin to PVP in the complex is more than 2.5, preferably more than 3, 4, 5, 7, 10 or 15.

The proportion (proportion by weight as well as the molar ratio) of hypericin in the total complex here should always be understood to be the mean proportion. A suitable method for determining the mean proportion of hypericin in the total complex is high performance liquid chromatography (HPLC). The person skilled in the art will be familiar with carrying out a determination of this type, as described in Freytag W. E. (Deutsche Apothekerzeitung 124 No. 46 (1984) 2383-2386). The person skilled in the art will know how to weigh an accurate quantity of hypericin-PVP complex, how to be able to determine the concentration from a calibration curve and an HPLC measurement and how to calculate the proportion by weight of hypericin in the total complex from it. An example of how a determination of this type can be carried out is described in Example 5.

Commercial PVP is available in a multitude of different degrees of polymerization and therefore of mean molar masses. Preferably, in the context of the present invention, molar masses in the range 10 kD to 40 kD are preferred, because molecules of this size can be excreted from the kidneys easily and without being metabolized (clearance).

Thus, in a preferred embodiment of the present invention, the hypericin-PVP complex is characterized in that the PVP has a mean molar mass of 10 to 40 kD, preferably from 12 to 25 kD.

Because of the small proportion of hypericin, the hypericin-PVP complexes described in the prior art are not suitable for use as ingredients in pharmaceutical compositions. In order to obtain sufficient quantities of hypericin for pharmaceutical applications, large quantities of the hypericin-PVP complex would have to be employed. This would lead to a disadvantageously high material consumption or an accumulation of PVP in the patient. This problem is solved with the present invention. Because of the greatly reduced proportion of adjuvants (PVP), higher dosages of water-soluble hypericin are possible; these are required for tumour therapy. More severe side effects of PVP can thus be avoided. The novel invention thus, inter alia, enables hypericin to be used in photodynamic tumour therapy.

Thus, the present invention also concerns a pharmaceutical composition comprising the hypericin-PVP complex in accordance with the invention.

In a preferred embodiment of the invention, the pharmaceutical composition is characterized in that the composition contains the hypericin-PVP complex in accordance with the invention with hypericin in a concentration of at least 25 mg/L, preferably at least 50 mg/L, 75 mg/L, 100 mg/L, 150 mg/L, or at least 250 mg/L.

In the context of the present invention, the "pharmaceutical compositions" may, for example, be administered locally for the treatment of tumours. In this manner, because the present invention means that for the first time, pharmaceutical compositions can be produced which contain high concentrations of hypericin without having to use large quantities of PVP, the present invention can also be used for pharmaceutical compositions which can be administered intravenously. Thus, large quantities of hypericin which subsequently become concentrated in tumour cells can also be administered systemically.

In a further preferred embodiment, the present invention therefore concerns a pharmaceutical composition containing the hypericin-PVP complex in accordance with the invention, characterized in that the composition is provided for intravenous administration.

In a particularly preferred embodiment, the present invention concerns a pharmaceutical composition containing the hypericin-PVP complex in accordance with the invention, characterized in that the composition is provided for intravenous administration and in that the composition contains hypericin in a concentration of at least 25 mg/L, preferably at least 50 mg/L, 60 mg/L, 80 mg/L, 100 mg/L, 150 mg/L, or at least 250 mg/L.

PVP, an amorphous substance, does not have a melting point but has what is known as a glass transition temperature. The glass transition temperature is dependent on the degree of polymerization, inter alia, i.e. on the mean molar mass of PVP (see Table 1).

TABLE 1

Examples for the glass transition temperature of PVP as a function of the molar mass

| PVP molar mass | Glass transition temperature |
|---|---|
| 12 kD | 93° C. |
| 17 kD | 130° C. |
| 25 kD | 155° C. |
| 30 kD | 175° C. |

In the experimental studies carried out during the development of the present invention, it was unexpectedly shown that a particularly high proportion by weight of hypericin in the hypericin-PVP complex can be obtained when a mixture of hypericin and polyvinylpyrrolidone is heated to a temperature which is above the glass transition temperature of the PVP employed. Hypericin is stable up to 300° C. and can thus be complexed with PVP as an intact molecule. This method therefore allows the hypericin-PVP complex in accordance with the invention to be produced.

Thus, the present invention also concerns a method for the production of the hypericin polyvinylpyrrolidone complex in accordance with the invention, characterized in that a mixture of hypericin and PVP is heated to a temperature which is above the glass transition temperature of the PVP employed.

In this context, the term "glass transition temperature of the PVP employed" should be understood to mean the temperature at which the glass transition of PVP in the pertinent mixture with hypericin occurs. The glass transition temperature of the PVP employed can be influenced by the composition of the mixture, for example when solvent or water is added to the mixture. Methods for determining the glass transition temperature are known to the person skilled in the art. Preferably, the glass transition temperature can be determined using the method of the appropriate DIN standard.

A preferred embodiment of the method for the production of the hypericin-PVP complex in accordance with the invention is characterized in that the molar mass of the PVP employed is at least 12 kD and the mixture is heated to a temperature of at least 93° C.

A particularly preferred embodiment is characterized in that the molar mass of the PVP employed is at least 17 kD and the mixture is heated to a temperature of at least 130° C.

A further particularly preferred embodiment is characterized in that the molar mass of the PVP employed is at least 25 kD and the mixture is heated to a temperature of at least 155° C.

A further particularly preferred embodiment is characterized in that the molar mass of the PVP employed is at least 35 kD and the mixture is heated to a temperature of at least 175° C.

It has been shown to be advantageous to add a solvent or a mixture of solvents to the mixture of hypericin and PVP. Preferably, the mixture of hypericin and PVP is stirred to form a paste in a little solvent. Additional solvents can contribute to distributing the components homogeneously and larger quantities of hypericin can be added to the PVP. Examples of suitable solvents are water, ethanol, methanol, pyridine, acetone, ethylmethylketone and pyridine, or mixtures thereof. Water, ethanol, methanol and pyridine are particularly preferred, especially water and ethanol.

Accordingly, a preferred embodiment of the method in accordance with the invention for the production of the hypericin-PVP complex is characterized in that a solvent or a mixture of solvents, preferably water, ethanol, methanol, pyridine, acetone, ethylmethylketone and/or ethyl acetate, more preferably water, ethanol, methanol and/or pyridine, yet more preferably water and/or ethanol, is added to the mixture of hypericin and PVP.

In the production method, it has been shown to be advantageous to maintain the mixture of hypericin and PVP for a specific period of time at a temperature which is above the glass transition temperature of the PVP employed. Good results were obtained when the mixture was held above the glass transition temperature for at least 5 minutes.

Accordingly, a preferred embodiment of the method in accordance with the invention for the production of the hypericin-PVP complex is characterized in that the mixture is maintained at a temperature which is above the glass transition temperature of the PVP employed for at least 5 minutes.

In the past 50 years, photodynamic therapy (PDT) of tumour diseases has developed rather on the fringes of oncology. However, the mechanisms of PDT have been extensively elucidated and methods are known in the prior art. Until now, however, there has been a dearth of genuinely suitable photosensitizers which are concentrated in tumour cells, which are highly compatible and which meet the physical and chemical requirements for PDT. The present invention provides hypericin-PVP complexes which meet these requirements and which, because of the high proportion of hypericin, are highly suitable for therapeutic applications. Because of this, the hypericin-PVP complexes in accordance with the invention can be administered either locally or systemically.

Thus, the present invention also concerns pharmaceutical compositions containing a hypericin-PVP complex in accordance with the invention for use in a therapeutic method, preferably for application in photodynamic therapy (PDT) for the treatment of tumour diseases.

The present invention also concerns a method for the treatment of cancer diseases, characterized in that a hypericin-PVP complex is administered, preferably during the course of photodynamic therapy (PDT).

In a preferred embodiment, the present invention provides a method for the treatment of cancer diseases, comprising the following steps:
  providing a pharmaceutically acceptable formulation containing a hypericin-PVP complex in accordance with the invention; and
  administering an effective quantity of this composition to a person who has cancer.

Preferably, the method for the treatment of cancer diseases includes irradiation of the person with light as an additional step. Preferably, the light has a wavelength between 400 nm and 800 nm, in particular between 500 nm and 700 nm, more preferably between 550 nm and 650 nm. Preferably, the light has an intensity between 1 mW/cm$^2$ and 250 mW/cm$^2$, particularly preferably between 2 mW/cm$^2$ and 100 mW/cm$^2$, more preferably between 3 mW/cm$^2$ and 50 mW/cm$^2$, most preferably between 5 mW/cm$^2$ and 25 mW/cm$^2$.

In combination with light, hypericin has an antiviral and antibacterial action. Thus, the complex in accordance with the invention can also be used for sterilising and/or disinfecting surfaces or liquids. The high proportion of hypericin in the hypericin-PVP complex is a significant advantage in this regard, because in this manner, the consumption of PVP is minimized.

Thus, the present invention also concerns the use of a hypericin-PVP complex in accordance with the invention for sterilising and/or disinfecting surfaces or liquids.

"Hypericin-PVP" or "hypericin-PVP complex" as used herein refers to a product which contains hypericin and PVP, and wherein a compound between hypericin and PVP molecules is formed. The word "complex" does not in any way limit the type of compound, but simply means that a compound is formed between one or more hypericin molecules and one or more PVP molecules. The compound may, for example, be a non-covalent addition of hypericin to PVP. The product as a whole and not an individual hypericin-PVP complex on a molecular level should be understood to be meant by "hypericin-PVP" or "hypericin-PVP complex".

The descriptions "proportion of complex", "proportion by weight", "molar ratio" as used herein should always be understood to refer to the mean values. They do not refer to any individual complex on a molecular level, but refer to a mean value for the product as a whole.

The present invention will be illustrated by the following examples and figures, which clearly do not limit the invention.

In the figures:

FIG. 1: Proportion by weight of hypericin in the total complex in two hypericin-PVP complexes in accordance with the invention compared with a conventional hypericin-PVP complex. The PVP employed for the complex in accordance with the invention was a PVP with a mean molar mass of either 12 kD ("HypPVP12 melt") or 25 kD ("HypPVP25 melt"). The PVP used for the production of the conventional complex was PVP with a mean molar mass of 25 kD ("HypPVP25 dissolved"). The complexes in accordance with the invention were produced as described in Example 1. The conventional complex was produced as described in Example 3.

Figure 2:
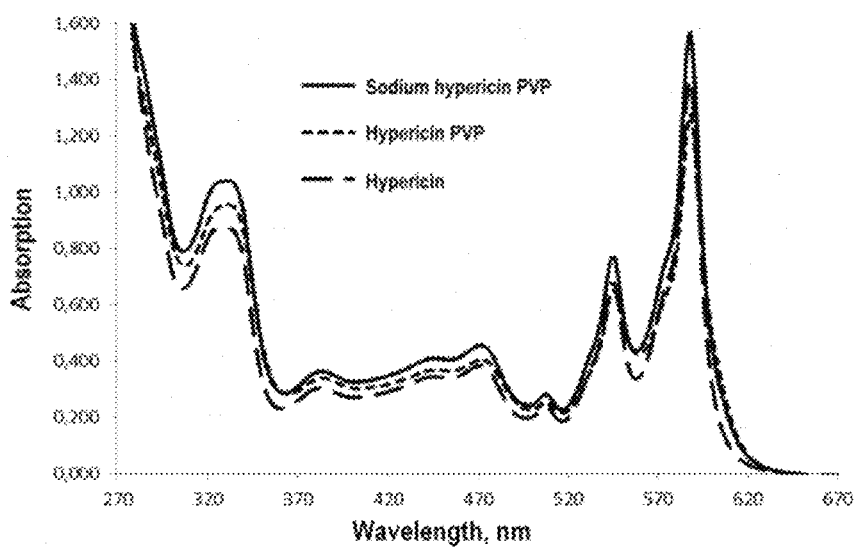

FIG. 2: Comparison of absorption spectra of sodium-hypericinate-PVP, hypericin-PVP and hypericin. The photophysical properties of hypericin were retained in the PVP complex, independently of whether the free acid or the sodium salt of hypericin was employed, or whether hypericin was present in the complexed form. This means that hypericin does not lose its photophysical properties in the form which is complexed by PVP.

FIG. 3: Calibration curve for the determination of the proportion by weight of hypericin with respect to hypericin-PVP complex by HPLC. HPLC runs were carried out as described in Example 5 with different quantities of hypericin. The concentration of the weighed hypericin (x axis) was plotted against the area of the absorption peak at 588 nm and a linear regression was generated.

EXAMPLE 1—Production of a Hypericin-PVP Complex in Accordance with the Invention 30 mg of polyvinylpyrrolidone (PVP 25 kD) was dry mixed with 15 mg of hypericin (99%, HPLC). 200 μL (200 microlitre equals 0.2 mL) of ethanol and 100 μL of water (100 microlitre equals 0.1 mL) were added to the mixture. Next, the mixture was stirred and allowed to stand for 20 minutes. After this, the mixture was heated slowly in a drying cabinet to 180° C. The temperature was programmed to rise from room temperature to 180° C. over a time period of approximately 20 minutes. The mixture was maintained at a temperature of 180° C. for approximately 8 minutes. After this, the mixture was cooled to room temperature. Next, approximately 3-6 mL of water was added and stirring was carried out for 1 hour. This caused the soluble components, the hypericin-PVP complex, to be taken up into solution. The insoluble components and the uncomplexed hypericin were filtered off (pore diameter 0.2-0.4 µm). The filtrate was dried and stored dry for further use.

EXAMPLE 2—Production of a Hypericin-PVP Complex in Accordance with the Invention Containing Hypericin in the Form of the Sodium Salt As for Example 1, except that instead of hypericin, the sodium salt was used: Na hypericinate. Na hypericinate was produced according to the instructions given by Kapinus et al. (Monatshefte für Chemie 130 (1999) 436-441).

EXAMPLE 3—Production of a Hypericin-PVP Complex According to the Prior Art

A conventional hypericin-PVP complex was produced as described by Kubin et. al. "How to make hypericin water-soluble", Die Pharmazie 63 (2008) 263-269. In this regard, 10 mg of hypericin was dissolved in 2.5 mL of ethanol using ultrasound, and thereafter, 1000 mg of PVP 25 kD and 8 mL of distilled water were added. The mixture was heated to 70° C. for approximately 5 minutes. Thereafter, 5 mL of water was added and the mixture was stirred for a further 10 minutes. The solution was then dried in a rotary evaporator and the hypericin-PVP complex obtained was stored dry for further use.

Upon attempting to add more hypericin to the complex, a precipitate was formed because under these conditions, it is not possible to form any complexes with PVP from substantially larger quantities of hypericin.

EXAMPLE 4—Characterization of the Hypericin-PVP Complexes

Hypericin-PVP complexes were produced in accordance with the method described in Examples 1 to 3.

The proportion by weight of hypericin in the hypericin-PVP complexes was determined using HPLC and using the appropriate calibration of hypericin. The reference material used was standardized hypericin (>99%, Planta Naturstoffe Vertriebs GmbH). The determination of the proportion by weight of hypericin in the total complex was carried out as described in Example 5.

In the complexes in accordance with the invention, proportion by weights of up to 40% by weight (hypericin free acid; production in accordance with Example 1) or 41% by weight (sodium hypericinate; production in accordance with Example 2) were measured, while the proportion by weight of the conventional complex was 1% by weight (production in accordance with Kubin et. al., Die Pharmazie 63 (2008) 263-269, as described in Example 3). By using the method in accordance with the invention, therefore, PVP could be loaded with almost 40 times the quantity of hypericin.

EXAMPLE 5—Determination of the Proportion by Weight of Hypericin in the Total Complex The proportion by weight of hypericin in the hypericin-PVP complexes was determined using HPLC and using the appropriate calibration with hypericin. The HPLC method was carried out substantially as described by Freytag W. E. (Deutsche Apothekerzeitung 124 No. 46 (1984) 2383-2386).

In detail, the HPLC method was carried out with:
eluent: 568.0 g methanol, 157.8 g ethyl acetate, 185.5 g buffer (13.8 g $NaH_2PO_4H_2O$ in 1000 mL of distilled water with 85% ortho-phosphoric acid at a pH of 2.1)
column: Nucleosil 120 3C18 (120 mm long, 4 mm internal diameter)
flow rate: 0.6 mL/min
detection: UV-vis at 588 nm.

For the calibration, standardized hypericin (>99%, Planta Naturstoffe Vertriebs GmbH) was used a reference material. HPLC runs with different quantities of reference material dissolved in HPLC eluent were carried out and the area of the hypericin absorption peak was determined at 588 nm. A calibration curve was generated from the measured values by means of a linear regression (see FIG. 3).

In order to determine the proportion of hypericin of a hypericin-PVP complex produced in accordance with Example 1, exactly 5 mg was weighed out from the dried hypericin-PVP complex (powder) and dissolved in HPLC eluent. A HPLC run was carried out as described above and the proportion of hypericin in the total complex was determined with the aid of the previously constructed calibration curve from the absorption signal obtained at 588 nm. The result obtained was 40% by weight (i.e. 100 mg of hypericin-PVP complex contained, for example, 40 mg of hypericin and 60 mg of PVP).

The invention claimed is:

1. A method for the production of a complex comprising polyvinylpyrrolidone (PVP) and hypericin or a hypericin salt, the method comprising, providing a mixture of hypericin or a hypericin salt and PVP, and heating the mixture to a temperature which is above a glass transition temperature of the PVP to form the complex,
wherein the complex comprises greater than 6% by weight of the hypericin or the hypericin salt with respect to a total weight of the complex.

2. The method as claimed in claim 1, wherein a solvent selected from the group consisting of water, ethanol, methanol, pyridine, acetone, ethylmethylketone, and/o ethyl acetate, and mixtures thereof is added to the mixture of hypericin and PVP.

3. The method as claimed in claim 1, wherein the mixture is maintained at a temperature greater than the glass transition temperature of the PVP for at least 5 minutes.

4. The method of claim 1, wherein a mean molar ratio of the hypericin or the hypericin salt to the PVP in the complex is greater than 2.5.

5. The method of claim 1, wherein the PVP has a mean molar mass of 10 to 40 kD.

* * * * *

UNITED STATES PATENT AND TRADEMARK OFFICE
CERTIFICATE OF CORRECTION

| | | |
|---|---|---|
| PATENT NO. | : 12,150,993 B2 | Page 1 of 1 |
| APPLICATION NO. | : 17/255349 | |
| DATED | : November 26, 2024 | |
| INVENTOR(S) | : Andreas Kubin | |

It is certified that error appears in the above-identified patent and that said Letters Patent is hereby corrected as shown below:

In the Claims

In Claim 2,
At Column 10, Line 47, delete "and/o"

Signed and Sealed this
Tenth Day of June, 2025

Coke Morgan Stewart
*Acting Director of the United States Patent and Trademark Office*